United States Patent [19]

Sestanj et al.

[11] 4,093,713
[45] June 6, 1978

[54] DIPEPTIDE DERIVATIVES WITH CENTRAL NERVOUS SYSTEM ACTIVITY AND PREPARATION THEREOF

[75] Inventors: Kazimir Sestanj, Pointe Claire; Hans Ueli Immer, Mount Royal; Manfred Karl Gotz, Hudson, all of Canada

[73] Assignee: Ayerst McKenna & Harrison Ltd., Montreal, Canada

[21] Appl. No.: 772,389

[22] Filed: Feb. 28, 1977

[51] Int. Cl.² ............................................. A61K 37/00
[52] U.S. Cl. ................................ 424/177; 260/326.2; 424/274
[58] Field of Search ...................... 260/112.5 R, 326.2; 424/177

[56] References Cited

U.S. PATENT DOCUMENTS 4,018,912   4/1977   Failli et al. .................... 260/112.5 R

*Primary Examiner*—Delbert R. Phillips
*Attorney, Agent, or Firm*—Stephen Venetianer

[57] ABSTRACT

The dipeptide derivatives of formula I

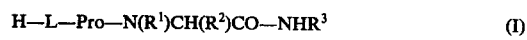

in which $R^1$, $R^2$ and $R^3$ each independently is lower alkyl and a method for their preparation are disclosed. The dipeptide derivatives of formula I possess central nervous system activity and methods for their use are given.

18 Claims, No Drawings

DIPEPTIDE DERIVATIVES WITH CENTRAL NERVOUS SYSTEM ACTIVITY AND PREPARATION THEREOF

BACKGROUND OF THE INVENTION (a) Field of Invention

The present invention relates to dipeptide derivatives with central nervous system activity, to a process for their preparation, and to intermediates therefor.

(b) Description of the Prior Art

The main obstacle to the practical use of many biologically active peptides is their brief period of action which is partly due to their inactivation by proteolytic enzymes. An example of such a peptide is the tripeptide which is the factor inhibiting release of the melanocyte stimulating hormone (MIF or MRIH).

This tripeptide was isolated from bovine hypothalamic tissue by R. M. G. Nair et al., Biochem. Biophys. Res. Commun., 43, 1376(1971) and its structure was established as the C-terminal tripeptide of oxytocin: H-L-prolyl-L-leucyl-glycinamide.

This tripeptide was shown to exert an action on the central nervous system (CNS). The tripeptide potentiates the behavioral effects of (3,4-dihydroxyphenyl)-L-alanine (L-DOPA) as shown by N. P. Plotnikoff et al., Life Sciences, 10, part 1, 1279(1971) and E. Friedman et al., Science, 182, 831(1973). The tripeptide antagonizes the effects of oxotremorin [N. P. Plotnikoff et al., Proc. Soc. Exp. Biol. Med., 140, 811(1972)] and reverses the sedative effects of deserpidine in mice and monkeys [N. P. Plotnikoff et al., Neuroendocrinology, 11, 67(1963)]. On the basis of the above biological activities A. V. Schally et al., Science 179, 341(1973) have suggested that the tripeptide H-Pro-Leu-Gly-$NH_2$ could be useful in the treatment of patients suffering from depression and parkinsonism.

Since the elucidation of the structure of the above tripeptide, a limited number of analogs of this peptide have been synthesized by M. E. Celis et al., Febs Letters, 27, 327(1972) and S. Castensson et al., Febs Letters, 44, 101(1974). However, the natural tripeptide and the analogs known to data have a short duration of action due to rapid inactivation in the mammalian body. Moreover, T. W. Redding et al., Neuroendocrinology, 11, 92(1973) have demonstrated that the first step in the inactivation of the natural tripeptide appears to be proteolytic cleavage of the Pro-Leu bond with formation of proline and leucyl-glycinamide.

Accordingly, analogs of the natural tripeptide having a greater resistance to protease hydrolysis while retaining the CNS activity of the natural tripeptide are of interest. The present invention discloses novel dipeptide analogs of the natural tripeptide in which: the leucyl amino acid residue may be replaced, the glycine amide portion is replaced with an alkyl amine and the peptide linkage is substituted with an alkyl group.

In addition, an unique and straightforward process for preparing these dipeptide derivatives is disclosed.

SUMMARY OF THE INVENTION

The peptide derivatives of this invention are represented by formula 1

H—L—Pro—N($R^1$)CH($R^2$)CO—NH$R^3$    (1)

in which $R^1$, $R^2$ and $R^3$ each independently is lower alkyl, or a therapeutically acceptable acid addition salt thereof.

The preferred peptide derivatives of this invention are represented by formula 1

H—L—Pro—N($R^1$)CH($R^2$)CO—NH$R^3$    (1)

in which $R^1$ and $R^3$ each independently is lower alkyl containing one to two carbon atoms and $R^2$ is lower alkyl containing one to four carbon atoms, or a therapeutically acceptable acid addition salt thereof.

The compounds of formula I are prepared by a process, which comprises removing the α-amino protecting group from the corresponding compound of formula II $R^4$—L—Pro—N($R^1$)CH($R^2$)CO—NH$R^3$    (II)

in which $R^1$, $R^2$ and $R^3$ are as defined herein and $R^4$ is an α-amino protecting group.

One embodiment for the preparation of the compound of formula II in which $R^1$, $R^2$, $R^3$ and $R^4$ are as defined herein comprises condensing together the following four components: (1) an α-amino protected proline derivative of the formula $R^4$—L—Pro—OH in which $R^4$ is as defined herein, (2) an alkyl amine of the formula $R^1$—$NH_2$ in which $R^1$ is as defined herein, (3) an aldehyde of the formula $R^2$—CHO in which $R^2$ is as defined herein, and 4) an isocyanide of the formula $R^3$—N ≡ C in which $R^3$ is as defined herein.

Another embodiment for the preparation of the compound of formula II in which $R^1$, $R^2$, $R^3$ and $R^4$ are as defined herein comprises condensing together the following three components: (1) an α-amino protected proline derivative of the formula $R^4$—L—Pro—OH in which $R^4$ is as defined herein, (2) an enamine of the formula $R^1$N = CH$R^2$ in which $R^1$ and $R^2$ are as defined herein and (3) an isocyanide of the formula $R^3$—N ≡ C in which $R^3$ is as defined herein.

Still another embodiment for the preparation of the compound of formula II in which $R^1$, $R^2$, $R^3$ and $R^4$ are as defined herein comprises the steps of: dehydrative coupling an α-amino protected proline derivative of the formula $R^4$—L—Pro—OH in which $R^4$ is as defined herein with a compound of the formula $H_2$N—CH($R^2$)CO—O$R^5$ in which $R^2$ is as defined herein and $R^5$ is lower alkyl to obtain the corresponding compound of the formula $R^4$—L—Pro-NHCH($R^2$)CO—O$R^5$ in which $R^2$, $R^4$ and $R^5$ are as defined herein, alkylating the latter compound with a compound of the formula $R^1$—X in which $R^1$ is as defined herein and X is a halogen selected from bromine, chlorine and iodine in the presence of an inorganic proton acceptor to obtain the corresponding compound of the formula $R^4$—L—Pro—N($R^1$)CH($R^2$)CO—O$R^5$ in which $R^1$, $R^2$, $R^4$ and $R^5$ are as defined herein and amidating the latter compound with an amine of the formula $R^3$—$NH_2$ in which $R^3$ is as defined herein.

Another aspect of this invention involves a method of treating or managing central nervous system disorders in a mammal which comprises administering to said mammal an effective amount of a compound of formula I, or a therapeutically acceptable acid addition salt thereof.

Still another aspect of this invention involves a pharmaceutical composition comprising a compound of formula I, or a therapeutically acceptable acid addition salt thereof, and a pharmaceutically acceptable carrier.

DETAILS OF THE INVENTION

The term "lower alkyl" as used herein contemplates straight chain alkyl radicals containing from one to six carbon atoms and branched chain alkyl radicals containing three to four carbon atoms excluding t-butyl and includes methyl (Me), ethyl (Et), propyl, isopropyl, butyl, isobutyl, pentyl and the like.

The term "moderately acidic conditions" as used herein contemplates conditions in which concentrated organic acids or aqueous solutions of a mineral acid are used as a principal component of the reaction medium at temperatures ranging from about −30° to 30° C. Examples of preferred conditions in this case include the use of 50 to 100% trifluoroacetic acid at 0° to 30° C, 0.1 to 12N hydrochloric acid at −30° to 10° C or 0.1 to 6N hydrogen chloride in an anhydrous inert organic solvent.

The term "organic proton acceptor" as used herein includes triethylamine, N-ethylmorpholine and N-ethyldiisopropylamine.

The term "inorganic proton acceptor" as used herein includes sodium hydride, potassium t-butoxide, sodium methoxide and the like.

In general the abbreviations used herein for designating the amino acids and the protective groups are based on recommendations of the IUPAC-IUB Commission on Biochemical Nomenclature see Biochemistry, 11, 1726 − 1732(1972). For instance Pro, Leu and Gly represent "residues" of proline, leucine and glycine, respectively. The term "residue" means a radical derived from the corresponding α-amino acid by eliminating the OH portion of the carboxyl group and a hydrogen of the α-amino group. The term "amino acid side chain" is that part of an amino acid exclusive of the —CH(NH$_2$-)COOH portion, as defined by K. D. Kopple, "Peptides and Amino Acids", W. A. Benjamin Inc., New York and Amsterdam, 1966, pages 2 and 33; an example of such a side chain of an amino acid is —CH$_2$CH(CH$_3$)$_2$ (the side chain of leucine).

The configurations of the amino acids and amino acid residues herein are designated by the appropriate symbols D, L or DL, furthermore when the configuration is not designated the amino acid or residue can have the configuration D, L or DL. It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis.

A number of procedures or techniques for the preparation of peptides have hitherto been well established and found in general textbooks of peptide chemistry; for example K. D. Kopple, supra, pp. 33–51 and E. Schroder and K. L. Lubke, "The Peptides"; Vol. 1; Academic Press, New York, 1965, pp. 3–128. For instance, the functional groups which are not involved in the peptide bond formation reaction are optionally protected by a protecting group or groups prior to the condensation reaction. Examples of protecting groups for an amino function of a peptide or amino acid not involved in the peptide bond formation are: the alkoxycarbonyls which incude benzyloxycarbonyl (represented by Z), t-butoxycarbonyl (represented by Boc), α,α-dimethyl-3,5-dimethoxybenzyloxycarbonyl (represented by Ddz), 2-(p-biphenyl)-isopropyloxycarbonyl (represented by Bpoc), p-chlorobenzyloxycarbonyl, p-methoxybenzyloxycarbonyl, isopropyloxycarbonyl, or ethoxycarbonyl; the acyl type protecting groups which include formyl, trifluoroacetyl, phthalyl, acetyl (Ac), or toluenesulfonyl; the alkyl type protecting groups which include triphenylmethyl or trityl (represented by Trt) or benzyl; the preferred protecting groups of this invention are benzyloxycarbonyl, t-butoxycarbonyl, triphenylmethyl and α, α-dimethyl-3,5-dimethoxy-benzyloxycarbonyl. The carboxylic acid function of a peptide or amino acid can be considered protected by a lower alkyl or lower aralkyl ester which includes methyl (represented by OMe), ethyl (OEt), benzyl (OBzl) or tert-butyl (OBu$^t$).

A peptide or amino acid is coupled with another peptide or amino acid to form a new peptide by the elimination of water (i.e. dehydrative coupling). More specifically, the OH portion of a peptide or amino acid having a free carboxyl group and the H portion of a peptide or amino acid having a free amino group are eliminated to form a new amide bond joining the peptide or amino acid starting materials. To promote facile condensation of a peptide free carboxyl group with a free amino group of another peptide to form a new peptide bond, the free carboxyl group must be activated. Descriptions of such carboxyl activating groups are included in the general textbooks of peptide chemistry by Kopple, or Schroder and Lubke, cited above. Examples of the activated form of a carboxyl are acid chloride, anhydride, azide, imidazolide, activated ester or O-acyl urea of a dialkylcarbodiimide (i.e. cyclohexylcarbodiimide). The following activated esters have proved to be particularly suitable in the process of this invention: 2,4,5-trichlorophenyl (represented by OTcp), pentachlorophenyl (OPcp), p-nitrophenyl(ONp), or 1-benzotriazolyl; the succinimido derivative is also useful for this purpose.

The coupling of a peptide or amino acid having the activated carboxyl with the peptide or amino acid having a free amino group is conducted in an inert organic solvent at a temperature from −30° C to about 50° C. For coupling to occur, the amino group must not be protonated. A sufficient amount of an organic proton acceptor is added to the above reaction mixture until the amino group is no longer protonated (usually pH 7.2 to 8.0).

The terms "peptide, dipeptide, tripeptide, and the like" used herein are not limited to refer to the respective parent peptides but also are used in reference to modified peptides having functionalized or protecting groups. The term "peptide" as used herein can be used in reference to a peptide with one to three amino acid residues.

The dipeptides of this invention are obtained in the form of the free base or as an acid addition salt directly from the process of this invention. The dipeptides in the form of the free bases are readily obtained from the corresponding acid addition salt by conventional methods, for example a solution of the acid addition salt is passed through an anionic exchange resin (OH-form) to obtain the free base. The free base is also obtained from the acetic acid addition salt by repeated lyophilization of the latter salt from aqueous solution. The acetic acid addition salt is readily obtained from another acid addition salt by treatment with the appropriate ion exchange resin in the manner hereinafter disclosed. The dipeptides of this invention are obtained in the form of a therapeutically acceptable acid addition salt either directly from the process of this invention or by reacting the dipeptide with one or more equivalents of the appropriate acid. Examples of preferred non toxic salts are those with therapeutically acceptable organic acids, e.g. acetic, lactic, succinic, benzoic, salicyclic, methanesulfonic, toluenesulfonic, or pamoic acid, as well as polymeric acids such as tannic acid or carboxymethyl cellulose, and salts with inorganic acids such as the hydrohalic acids, e.g. hydrochloric acid, or sulfuric acid, or phosphoric acid. If desired a particular acid addition salt is converted into another acid addition salt, e.g., a salt with a non toxic, pharmaceutically acceptable acid, by treatment with the appropriate ion exchange resin in the manner described by R. A. Boissonas, et al., Helv. Chim. Acta, 43, 1349(1960). Suitable ion exchange resins are cellulose based cation exchangers, for example carboxymethylcellulose, or chemically modified, cross-linked dextran cation exchangers, for example, those of the Sephadex C type, and strongly basic anion exchange resins, for example those listed in J. P. Greestein and M. Winitz "Chemistry of the Amino Acids", John Wiley and Sons, Inc., New York and London, 1961, Vol. 3, p. 1456.

The dipeptide derivatives produced by the process of this invention, as well as their corresponding therapeutically acceptable salts, are useful because they show the pharmacological activities upon the CNS of mammals possessed by the natural tripeptide H-L-prolyl-L-leucylglycinamide. For example, the compounds of this invention potentiate the effects of L-DOPA when tested by the method G. M. Everett, Proc. First Internat. Sympos. Antidepr. Drugs, Excepta Medica Internat. Congr. Series no. 122, 164(1966) in the modification described by N. P. Olotnikoff et al., Life Sciences Vol. 10, Part 1, p 1279(1971). The dipeptide derivatives of formula I also antagonize fluphenazineinduced catalepsy in rats, an animal model particularly suitable for screening compounds useful in the management of Parkinson-like disorders, and they cause reversal of the sedative effect of deserpidine, an animal model of depression. The dipeptide derivatives of this invention have a prolonged duration of action and are useful for treating or managing central nervous system disorders, especially Parkinsonism and mental depression, in mammals. When a dipeptide of this invention or a salt thereof is employed for such treatment or management, it is administered systemically, preferably parenterally, in combination with a pharmaceutically acceptable liquid or solid carrier. The dipeptides of formula I have a low order of toxicity. The proportion of the dipeptide or salt thereof is determined by its solubility in the given carrier, by the given carrier, by the chosen route of administration and by standard biological practice. For parenteral administration to mammals the dipeptide or a salt thereof is used in a sterile aqueous solution which may also contain other solutes such as buffers or preservatives, as well as sufficient therapeutically acceptable salts or glucose to make the solution isotonic. The dosage will vary with the form of administration and with the particular species of animal to be treated and is preferably kept at a level of from 0.05 mg to 20 mg per kilogram of body weight. However, a dosage level in the range of from about 0.05 mg to about 2 mg per kilogram of body weight is most desirably employed in order to achieve effective results.

For oral administration to a mammal the dosage of the dipeptide or a salt thereof is preferably kept at a level of from 0.25 mg to 100 mg per kilogram of body weight, and the compound is formulated in unit dosage form with pharmaceutically acceptable carriers. The dipeptide or a salt thereof may also be administered directly to the interior surface of the mouth, for example in one of the dosage forms described in U.S. Pat. No. 3,972,995, issued Aug. 3, 1976.

The dipeptide or a salt thereof may also be administered in one of the long acting, slow-release or depot dosage forms described below, preferably by intramuscular injection or by implantation. Such dosage forms are designed to release from about 0.05 mg to about 2 mg per kilogram body weight per day.

It is often desirable to administer a dipeptide of formula I continuously over prolonged periods of time in longacting, slow-release, or depot dosage forms. Such dosage forms may either contain a therapeutically acceptable salt of the dipeptide having a low degree of solubility in body fluids, for example one of those salts described below, or they may contain the dipeptide in the form of a water-soluble salt together with a protective carrier which prevents rapid release. In the latter case, for example, the dipeptide may be formulated with a non-antigenic partially hydrolyzed gelatin in the form of a viscous liquid; or the dipeptide may be absorbed on a pharmaceutically acceptable solid carrier, for example, zinc hydroxide, and may be administered in suspension in a pharmaceutically acceptable liquid vehicle; or the dipeptide may be formulated in gels of suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g. in Remington's Pharmaceutical Sciences, 14th Ed., Mack Publishing Co., Easton; Pennsylvania, 1970. Long-acting, slow-release preparations of the dipeptide produced according to the process of this invention may also be obtained by microencapsulation in a pharmaceutically acceptable coating, for example gelatine, polyvinyl alcohol or ethyl cellulose, Further examples of coating materials and of the processes used for microencapsulation are described by J. A. Herbig in "Encyclopedia of Chemical Technology", Vol. 13, 2nd Ed., Wiley, New York 1967, pp. 436–456. Such formulations, as well as suspensions of salts of the dipeptide which are only sparingly soluble in body fluids, for example the salt with pamoic acid, are designed to release from about 0.05 mg to about 2 mg of the active compound per kilogram of body weight per day, and are preferably administered by intramuscular injection. Alternatively, some of the solid dosage forms listed above, for example certain sparingly water-soluble salts or dispersions in or adsorbates on solid carriers of salt of the agent, for example dispersions in a neutral hydrogel of a polymer of ethylene glycol methacrylate or similar monomers cross-linked as described by K. Kliment et al., in U.S. Pat. No. 3,551,556, issued Dec. 29, 1970 may also be formulated in the form of pellets releasing about the same amounts as shown above and may be implanted subcutaneously or intramuscularly.

The dipeptide derivatives of formula I, or a therapeutically acceptable acid addition salt thereof, potentiate the therapeutic effectiveness of drugs used for the treatment of Parkinson's disease; for example, levodopa, procyclidine, 1-hyoscyamine or trihexyphenidyl hydrochloride.

Noteworthy is the finding that levodopa in combination with a dipeptide derivative of this invention manifests a greater improvement in motility and in intellectual functioning than levodopa alone.

When the derivatives of formula I are used to potentiate the effects of levodopa in humans, the derivative and levodopa are administered systemically, either separately or in the same unit dosage form; the combination being orally or parenterally effective. The usual daily dose for the derivative ranges 50 to 2000 mg and the daily dose of levodopa ranges from 0.5 to 8.0 g.

Typical pharmaceutical compositions, prepared in the manner described above for the dipeptide derivative along, comprise a combination of the dipeptide derivative of formula I and levodopa, in solid form or in sterile solutions, in a 1:4 to 1:160 ratio by weight.

PROCESS

The process of this invention is illustrated by the following description of preferred embodiments.

The practice of one embodiment of the process of this invention involves the condensation of the following four components: (1) an α-amino protected proline derivative of the formula $R^4$—L—Pro—OH in which $R^4$ is an α-amino protecting group, (2) an alkyl amine of the formula $R^1$—$NH_2$ in which $R^1$ is lower alkyl, (3) an aldehyde of the formula $R^1$—CHO in which $R^2$ is lower alkyl and (4) an isocyanide of the formula $R^3$—N ≡ C in which $R^3$ is lower alkyl to obtain the corresponding compound of formula II $$R^4\text{—L—Pro—}N(R^1)CH(R^2)CO\text{—}NHR^3 \quad (II)$$

in which $R^1$, $R^2$, $R^3$ and $R^4$ are as defined herein.

Although, not critical, it is preferable to use approximately equimolar amounts of the requisite starting materials for this condensation. The condensation is effected most conveniently in an inert organic solvent, for example, in halogenated hydrocarbons including methylene chloride, chloroform and carbon tetrachloride; in ethers and cyclic ethers including dioxane, diethyl ether and tetrahydrofuran; or in lower aliphatic alcohols including methanol, ethanol and propanol; methanol is the preferred inert organic solvent. However, when the starting materials are mutually soluble or the mixture thereof becomes liquid during the course of the condensation the solvent may be omitted without any deleterious effects.

The temperature and duration of the condensation are also not critical. The reaction may be performed at temperatures ranging from −20° to 100° C; however, a range from 10° to 40° C is most convenient. The reaction time may be varied and depends on the reactivity of the various starting materials; however, reaction times from 15 minutes to several days are employed generally, with six hours to two days being preferred.

Thereafter, the intermediate of formula II is isolated and purified according to standard procedures. For instance the product is extracted with a water-immiscible solvent and, if needed, purified by chromatography and crystallization.

It will be apparent to those skilled in the art that the portion of the compound of formula II represented by —$N(R^1)CH(R^2)CO$— as obtained in the reaction must be asymmetric. Consequently, it is apparent that the intermediate of formula II exists in the form of two diastereo-isomers which may be separated, for example by chromatography on silica gel and/or crystallization to obtain the two separate isomers of formula II illustrated by $R^4$—L—Pro—L—$N(R^1)CH(R^2)CO$—$NHR^3$ and $R^4$—L—Pro—D—$N(R^1)CH(R^2)CO$—$NHR^3$. The above mentioned portion represented by —$N(R^1)CH(R^2)CO$— may represent a N-alkyl amino acid residue, for example the compound of formula II in which $R^1$ is methyl and $R^2$ is $CH_2CH(CH_3)_2$ represents the dipeptide of the formula $R^4$—L—Pro— (N-methyl)-Leu—$NHR^3$.

A useful modification of the above condensation is to first condense equimolar amounts of the alkyl amine and the aldehyde in an inert solvent at an elevated temperature, at or near the reflux temperature of the mixture to obtain the corresponding enamine of the formula $R^1N = CHR^2$ in which $R^1$ and $R^2$ are as defined herein. Suitable inert solvents can be selected from an anhydrous, water-immiscible hydrocarbon solvent, for example, benzene or toluene, with concomitant physical removal of water as it is being formed, for instance, by means of a Dean-Stark water separator, or a lower alkanol solvent, for example, ethanol, propanol, or isopropanol. Thereafter, evaporation of the solvent and purification of the residue, for example by distillation or crystallization, yields the corresponding enamine. Subsequently, the enamine of the formula $R^1N = CHR^2$, the α-amino protected proline derivative of the formula $R^4$—L—Pro—OH and the isocyanide of the formula $R^3$—N ≡ C are condensed, in the same manner as described above for the four component condensation, to obtain the corresponding compound of formula II in which $R^1$, $R^2$, $R^3$ and $R^4$ are as defined herein.

Another embodiment for the preparation of the compound of formula II involves the classical techniques of peptide chemistry. In this embodiment, $R^4$—L—Pro—OH is coupled with a compound of formula $H_2N$—$CH(R^2)CO$—$OR^5$ in which $R^2$ and $R^5$ each independently is lower alkyl to obtain the corresponding compound of the formula $R^4$—L—Pro—$NHCH(R^2)CO$—$OR^5$ in which $R^2$, $R^4$ and $R^5$ are as defined herein. The preferred method of achieving this dehydrative coupling is to use the activated ester coupling method. A preferred procedure for achieving the latter coupling is to stir solution containing substantially equimolar amounts of $R^4$—L—Pro—OH, $N_2N$—$CH(R^2)CO$—$OR^5$, 1-hydroxybenzotriazole and dicyclohexylcarbodiimide in an inert solvent, preferably dimethylformamide or tetrahydrofuran, at −10° to 30° C for 10 to 30 hours. If required, an organic proton acceptor, preferably N-ethylmorpholine, is added to the solution to maintain a pH of 7.5 to 8.5. The product of the formula $R^4$—L—Pro—$NHCH(R^2)CO$—$OR^5$ is isolated by conventional methods.

In the latter condensation specific isomers of $H_2N$—$CH(R^2)CO$—$OR^5$ can represent an ester of an amino acid, for instance when $R^2$ is $CH_2CH(CH_3)_2$, the compound of the formula D—$H_2N$—$CH(R^2)CO$—$OR^5$ can be written as H—D—Leu—$OR^5$ and when $R^2$ is $CH_3$, the compound of formula L—$H_2N$—$CH(R^2)CO$—$OR^5$ can be written as H—L—Ala—$OR^5$.

Some of the compounds of the formula $R^4$—L—Pro—$NHCH(R^2)CO$—$OR^5$ and the process for preparing these compounds are described in publications. For example, the latter compound in which $R^2$ is $CH_2CH(CH_3)_2$, $R^4$ is Boc and $R^5$ is $CH_3$, i.e. Boc—L—Pro—D—Leu—OMe, is described in the publication by D. E. Nitecki et al., J. Org. Chem., 33, 864(1968).

In the next step, the compound of the formula $R^4$—L—Pro—NHCH($R^2$)—CO—$OR^5$ is alkylated, preferably with a compound of the formula $R^1$—X in which $R^1$ is as defined herein and X is bromine, chlorine, or iodine in the presence of an inorganic proton acceptor, to obtain the corresponding compound of the formula $R^4$—L—Pro—N($R^1$)CH($R^2$)CO—$OR^5$ in which $R^1$, $R^2$, $R^4$ and $R^5$ are as defined herein. A convenient method of achieving this alkylation is to stir a solution of the compound of the formula $R^4$—L—Pro—NHCH($R^2$)CO—$OR^5$ with two to five molar equivalents of the compound of the formula $R^1$—X in the presence of 1.1 to 2.0 molar equivalents of an inorganic proton acceptor, preferably sodium hydride, in a dry inert solvent, preferably tetrahydrofuran, dimethylformamide or mixtures thereof, at 50° to 90° C for two to ten hours.

The compound of the formula $R^4$—L—Pro—N($R^1$)CH($R^2$)CO—$OR^5$, obtained from the latter reaction, is amidated with an alkyl amine of the formula $H_2N$—$R^3$ in which $R^3$ is as defined herein. Preferred conditions for the amidation involves the reaction of $R^4$—L—Pro—N($R^1$)CH($R^2$)CO—$OR^5$ with 5 to 20 molar equivalents of the amine of the formula $H_2N$—$R^3$ in an inert organic solvent (i.e. methanol, ethanol and the like) at 20° to 50° C for 5 to 15 days. A pressure vessel may be required if the alkyl amine is volitile at the temperature necessary for reaction. The corresponding compound of formula II in which $R^1$, $R^2$, $R^3$ and $R^4$ are as defined herein is subsequently isolated by conventional means.

The compound of formula II

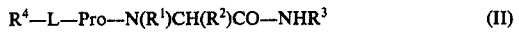

$$R^4—L—Pro—N(R^1)CH(R^2)CO—NHR^3 \quad (II)$$

in which $R^1$, $R^2$, $R^3$ and $R^4$ are as defined herein, obtained by a process described above, is deprotected by removal of the protecting group $R^4$ to obtain the corresponding compound of formula I

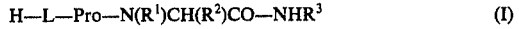

$$H—L—Pro—N(R^1)CH(R^2)CO—NHR^3 \quad (I)$$

in which $R^1$, $R^2$ and $R^3$ are as defined herein.

The conditions necessary for the removal of the α-amino protecting group $R^4$ are dependent upon the nature of the protecting group $R^4$. In general, the conditions chosen must not affect the remainder of the molecule, for example, asymetric centers must not be racemized and other chemical reactions must not occur.

The α-amino protecting group $R^4$ can be readily removed by the reaction of anhydrous hydrogen fluoride with the compound of formula II to obtain the corresponding compound of formula I as the hydrogen fluoride salt. The use of anhydrous hydrogen fluoride will remove the protecting group $R^4$ regardless of the nature of this group. On the other hand, the protecting group $R^4$ can be removed by selected reaction conditions dependent upon the nature of the protecting group $R^4$.

For example, the α-amino protecting group, benzyloxycarbonyl (i.e. $R^4$ = Z) is easily removed by reacting the compound of formula II in which $R^4$ is Z with hydrogen in the presence of a noble metal catalyst, for example 5 to 10% palladium or platinum on carbon. Suitable solvents for this hydrogenation include acetic acid, methanol, ethanol, ethyl acetate and the like. The selection of methanol, ethanol or ethyl acetate as a solvent will give the compound of formula I as the free base.

Other α-amino protecting groups $R^4$ can be selected so that they are removed under moderately acidic conditions. For example, the compound of formula II in which $R^4$ is t-butoxycarbonyl (Boc), α,α-dimethyl-3,5-dimethoxybenzyloxycarbonyl (Ddz) or 2-(p-biphenyl)isopropyloxycarbonyl (Bpoc) is deprotected under moderately acidic conditions to obtain the corresponding compound of formula I as the acid addition salt corresponding to the acid used. Examples of preferred conditions in this case include the use of 50 to 100% trifluoroacetic acid at 0° to 30° C, 0.1 to 12N hydrochloric acid at −30° to 10° C or 0.1 to 6N hydrogen chloride in an ahydrous inert organic solvent at −30° to 20° C. Using one of the latter conditions, the deprotection is usually completed after 15 minutes to three hours.

The compound of formula I in the form of an acid addition salt obtained from one of the above described deprotecting reactions using an acid is readily converted to the corresponding free base using an anionic exchange chromatography resin. Weakly basic anion exchanger resins are preferred. Examples of the latter resins are cross-linked polystyrene or modified dextran having substituted amine functional groups. The compound of formula I in the form of an acid addition salt is dissloved in water and/or methanol and passed through the resin in its basic form (OH). Evaporation of the eluates gives a residue containing the corresponding compound of formula I in the form of a free base.

The following examples illustrate further this invention.

EXAMPLE 1 t-Butoxycarbonyl-L-prolyl-D-N-methyl-leucine Ethyl Amide (II; $R^1$ = $CH_3$, $R^2$ = $CH_2CH(CH_3)_2$, $R^3$ = $CH_2CH_3$ and $R^4$ = Boc)

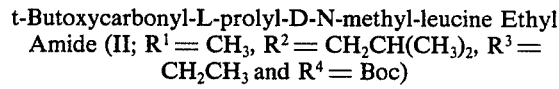

To a cooled (0° to 5° C), stirred solution of t-butoxycarbonyl-L-proline (6.54 g, 30.4 mmoles) in methanol (30 ml) is added a cold (0° to 5° C) solution of 3-methylbutanal (2.88 g, 3.67 ml) and methylamine (40% aqueous solution, 1.04 g, 2.62 ml) in methanol (19 ml) followed by ethyl isocyanide [1.84 g, 2.5 ml, described by J. Casanova et al., J. Chem. Soc., 4280(1963)]. The mixture is kept in an ice bath for 1 hour and at room temperature for 2 days. The reaction mixture is evaporated to dryness and the foamy residue is dissolved in methylene chloride (90 ml). The solution is washed with 5% citric acid (25 ml), brine (25 ml), 5% sodium bicarbonate (2×25 ml) and brine (25 ml). After drying over anhydrous magnesium sulfate and evaporation, the crude material is subjected to chromatography on silica gel using chloroform/ethyl acetate (9:1). The initial eluate fractions are evaporated and the residue is crystallized from hexane to obtain crystals of the title compound; mp 117°–119° C, $[\alpha]_D^{25°}$ + 54.9° (c = 1, dimethylformamide).

The latter eluate fractions are evaporated and the residue is crystallized from hexane to obtain crystals of t-butoxycarbonyl-L-prolyl-L-N-methyl-leucine ethyl amide; mp 101°–104° C, $[\alpha]_D^{25°}$ −67.2° (c = 1, dimethylformamide).

In the same manner but replacing methylamine with an equivalent amount of ethylamine, propylamine or pentylamine, the following compounds of formula II are obtained, respectively:
t-butoxycarbonyl-L-prolyl-D-N-ethyl-leucine ethyl amide, t-butoxycarbonyl-L-prolyl-L-N-ethyl-leucine ethyl amide, t-butoxycarbonyl-L-prolyl-D-N-propyl-leucine ethyl amide, t-butoxycarbonyl-L-prolyl-L-N-propyl-leucine ethyl amide, t-butoxycarbonyl-L-prolyl-D-N-pentyl-leucine ethyl amide and t-butoxycarbonyl-L-prolyl-L-N-pentyl-leucine ethyl amide.

Similarly, replacing ethyl isocyanide with an equivalent amount of methyl isocyanide, propyl isocyanide or 2-methyl-propyl isocyanide, the following compounds of formula II are obtained, respectively:

t-butoxycarbonyl-L-prolyl-D-N-methyl-leucine methyl amide,
t-butoxycarbonyl-L-prolyl-L-N-methyl-leucine methyl amide,
t-butoxycarbonyl-L-prolyl-D-N-methyl-leucine propyl amide,
t-butoxycarbonyl-L-prolyl-L-N-methyl-leucine propyl amide,
t-butoxycarbonyl-L-prolyl-D-N-methyl-leucine 2-methyl-propyl amide and
t-butoxycarbonyl-L-prolyl-L-N-methyl-leucine 2-methyl-propyl amide.

Similarly, replacing 4-methyl-butanal with an equivalent amount of acetaldehyde, 2-methyl-propanal or pentanal, the following compounds of formula II are obtained, respectively:

t-butoxycarbonyl-L-prolyl-D-N-methyl-alanine ethyl amide,
t-butoxycarbonyl-L-prolyl-L-N-methyl-alanine ethyl amide,
t-butoxycarbonyl-L-prolyl-D-N-methyl-valine ethyl amide,
t-butoxycarbonyl-L-prolyl-L-N-methyl-valine ethyl amide,
t-butoxycarbonyl-L-prolyl-D-N-methyl-norleucine ethyl amide and
t-butoxycarbonyl-L-prolyl-L-N-methyl-norleucine ethyl amide.

EXAMPLE 2 t-Butoxycarbonyl-L-prolyl-D-N-methyl-leucine Methyl Ester

Methyl iodide (8.45 g) is added to a solution of t-butoxycarbonyl-L-prolyl-D-leucine methyl ester [15.28 g, 0.0446 mole, described by D. E. Nituki et al., J. Org. Chem., 33, 864(1968)] in a mixture of dry tetrahydrofurandimethylformamide (10:1, 125 ml) followed by sodium hydride (0.785 g, 50% dispersion, 0.0163 mole). The mixture is stirred and heated in an oil bath (80° C) for 2 hours. Two more portions of methyl iodide and sodium hydride are added to the mixture at 2 hours intervals. Finally, a small amount of sodium hydride is added (217 mg, 0.00455 mole) and the reaction mixture is heated at 80° C for 1.5 hour. The solvent is evaporated and the residue is dissolved in ether (220 ml) and water (55 ml). The organic layer is separated, washed with water and dried over anhydrous magnesium sulfate. The solvent is evaporated and the residue is crystallized from boiling ether to give crystals of the title compound; mp 116°–119° C, $[\alpha]_D^{25°} + 21.8°$ C (c = 1, dimethylformamide).

In the same manner but replacing sodium hydride with an equivalent amount of sodium methoxide or potassium t-butoxide, the title compound is obtained.

In the same manner but replacing t-butoxycarbonyl-L-prolyl-D-leucine methyl ester with an equivalent amount of α,α-dimethyl-3,5-dimethoxybenzyloxycarbonyl-L-prolyl-D-alanine methyl ester or α,α-dimethyl-3,5-dimethoxybenzyloxycarbonyl-L-prolyl-D-valine methyl ester and replacing methyl iodide with an equivalent amount of ethyl iodide, the following compounds are obtained, respectively:

α,α-dimethyl-3,5-dimethoxybenzyloxycarbonyl-L-prolyl-D-N-ethylalanine methyl ester and α,α-dimethyl-3,5-dimethoxybenzyloxycarbonyl-L-prolyl-D-N-ethyl-valine methyl ester.

EXAMPLE 3 t-Butoxycarbonyl-L-prolyl-D-N-methyl-leucine Ethyl Amide (II; $R^1 = CH_3$, $R^2 = CH_2CH(CH_3)_2$, $R^3 = CH_2CH_3$ and $R^4 = $ Boc)

To a cooled solution (0° to 5° C) of t-butoxycarbonyl-L-prolyl-D-N-methyl-leucine methyl ester (1.0 g, 2.805 mmoles, described in Example 2) in methanol (5 ml) in a pressure bottle is added anhydrous ethylamine (2 ml, 1.3 g, 28.0 mmoles). The bottle is tightly closed and allowed to warm up to room temperature. After standing at room temperature for five days, more ethylamine (2 ml) is added and the reaction mixture is heated in an oil bath at 40°–45° C for four days. The mixture is evaporated and the residue is dissolved in methanol (10 ml). Sodium hydroxide (1N, 2 ml) solution is added and the solution is heated to 35° C for 1 hour. The solution is evaporated and a mixture of ether (30 ml) and water is added to the residue. The separated aqueous layer is extracted with ether and the combined organic layers is washed with brine. The organic solution is evaporated and the residue is crystallized from hexane to give crystals of the title compound; mp 116°–118° C, $[\alpha]_D^{25°} + 54.1$ (c = 1 dimethylformamide).

The title compound obtained by the process of this Example is identical to the title compound of Example 1.

In the same manner but replacing t-butoxycarbonyl-L-prolyl-D-N-methyl-leucine methyl ester with an equivalent amount of α,α-dimethyl-3,5-dimethoxybenzyloxycarbonyl-L-prolyl-D-N-ethyl-alanine methyl ester (described in Example 2) or α,α-dimethyl-3,5-dimethoxybenzyloxycarbonyl-L-prolyl-D-N-ethyl-valine methyl ester (described in Example 2) the following compounds of formula II are obtained, respectively:

α,α-dimethyl-3,5-dimethoxybenzyloxycarbonyl-L-prolyl-D-N-ethyl-alanine ethyl amide and α,α-dimethyl-3,5-dimethoxybenzyloxycarbonyl-L-prolyl-D-N-ethyl-valine ethyl amide.

EXAMPLE 4

L-Prolyl-D-N-methyl-leucine Ethylamide (1, $R^1 = CH_3$, $R^2 = CH_2CH(CH_3)_2$ and $R^3 = CH_2CH_3$)

A solution of the compound of formula II, t-butoxycarbonyl-L-prolyl-D-N-methyl-leucine ethyl amide (1.7 g, 4.6 mmoles), described in Example 1 or 3), in trifluoroacetic acid (5.3 g, 46 mmoles) is stirred at 0° to 5° C for one hour. The solution is evaporated to give a residue of the title compound in the form of a salt with trifluoroacetic acid. The residue is dissolved in methanol (30 ml) and the solution is passed through a column containing an anionic exchange resin ["Amberlite IR-45 (OH)", 75 ml, swelled in methanol overnight]. The column is washed with methanol and the eluates are combined and evaporated to give a residue of the title compound, n m r(CD$_3$OD) δ 0.85 – 1.35 (m, 9H) and 3.05 (s, 3H). The residue is dissolved in water (40 ml) and 0.1N aqueous sulfuric acid (43.3 ml) is added until pH 4.5 is reached. The solution is evaporated and the residue is crystallized from ethanol to give crystals of the sulfate salt of the title compound; mp 165° C (dec), $[\alpha]_D^{25°} + 11.77°$ (c = 1, methanol.

In the same manner but replacing t-butoxycarbonyl-L-prolyl-D-N-methyl-leucine ethyl amide with an equivalent amount of t-butoxycarbonyl-L-prolyl-L-N-methyl-leucine ethyl amide (described in Example 1), L-prolyl-L-N-methyl-leucine ethylamide, n m r(CD$_3$OD) δ 0.9 – 1.3 (m, 9H) and 2.97 – 3.08 (m, 3H), and L-prolyl-L-N-methyl-leucine ethylamide sulfate salt, $[\alpha]_D^{25°} -109.6°$ (c = 1, methanol), is obtained.

Similarly, replacing t-butoxycarbonyl-L-prolyl-D-N-methyl-leucine ethyl amide with an equivalent amount of another compound of formula II described in Example 1, the following compounds of formula I are obtained, respectively:
L-prolyl-D-N-ethyl-leucine ethyl amide,
L-prolyl-L-N-ethyl-leucine ethyl amide,
L-prolyl-D-N-propyl-leucine ethyl amide,
L-prolyl-L-N-propyl-leucine ethyl amide,
L-prolyl-D-N-pentyl-leucine ethyl amide,
L-prolyl-L-N-pentyl-leucine ethyl amide,
L-prolyl-D-N-methyl-leucine methyl amide,
L-prolyl-L-N-methyl-leucine methyl amide,
L-prolyl-D-N-methyl-leucine propyl amide,
L-prolyl-L-N-methyl-leucine propyl amide,
L-prolyl-D-N-methyl-leucine 2-methyl-propyl amide,
L-prolyl-L-N-methyl-leucine 2-methyl-propyl amide,
L-prolyl-D-N-methyl-alanine ethyl amide,
L-prolyl-L-N-methyl-alanine ethyl amide,
L-prolyl-D-N-methyl-valine ethyl amide,
L-prolyl-L-N-methyl-valine ethyl amide,
L-prolyl-D-N-methyl-norleucine ethyl amide and
L-prolyl-L-N-methyl-norleucine ethyl amide.

Again, similarly, replacing t-butoxycarbonyl-L-prolyl-D-N-methyl-leucine ethyl amide with an equivalent amount of another compound of formula II described in Example 3 and replacing trifluoroacetic acid with a mixture of formic acid-acetic acid-water (1:7:2), the following compounds of formula I are obtained, respectively:
L-prolyl-D-N-ethyl-alanine ethyl amide and
L-prolyl-D-N-ethyl-valine ethyl amide.

We claim:

1. A compound of formula I

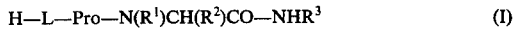

in which $R^1$, $R^2$ and $R^3$ each independently is lower alkyl, or a therapeutically acceptable acid addition salt thereof.

2. A compound of formula I

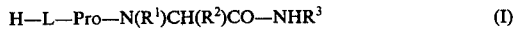

in which $R^1$ and $R^3$ each independently is lower alkyl containing 1 to 2 carbon atoms and $R^2$ is lower alkyl containing 1 to 4 carbon atoms, or a therapeutically acceptable acid addition salt thereof.

3. L-Prolyl-L-N-methyl-leucine ethylamide, as claimed in claim 2.

4. L-Prolyl-D-N-methyl-leucine ethylamide, as claimed in claim 2.

5. The sulfate salt of the compound of claim 3.

6. The sulfate salt of the compound of claim 4.

7. A compound of formula II

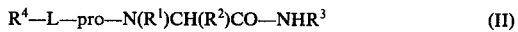

in which $R^1$, $R^2$ and $R^3$ each independently is lower alkyl and $R^4$ is an α-amino protecting group.

8. t-Butoxycarbonyl-L-prolyl-L-N-methyl leucine ethylamide, as claimed in claim 7.

9. t-Butoxycarbonyl-L-prolyl-D-N-methyl-leucine ethylamide, as claimed in claim 7.

10. A method of treating or managing central nervous system disorders in a mammal which comprises administering to said mammal an effective amount of a compound of formula I, as claimed in claim 1, or a therapeutically acceptable acid addition salt thereof.

11. The method as claimed in claim 10 wherein said compound is L-prolyl-L-N-methyl-leucine ethylamide.

12. The method as claimed in claim 10 wherein said compound is L-prolyl-D-N-methyl-leucine ethylamide.

13. A pharmaceutical composition comprising a compound of formula I or a therapeutically acceptable acid addition salt thereof, as claimed in claim 1, and a pharmaceutically acceptable carrier.

14. The pharmaceutical composition as claimed in claim 13 wherein said compound is L-prolyl-L-N-methyl-leucine ethylamide.

15. The pharmaceutical composition as claimed in claim 13 wherein said compound is L-prolyl-D-N-methyl-leucine ethylamide.

16. A pharmaceutical composition in unit dosage form for treating Parkinson's disease comprising a combination of a compound of formula I of claim 1, or a therapeutically acceptable acid addition salt thereof, together with a therapeutic dose of levodopa and a pharmaceutically acceptable carrier.

17. The pharmaceutical composition as claimed in claim 16 wherein said compound is L-prolyl-L-N-methyl-leucine ethylamide.

18. The pharmaceutical composition as claimed in claim 16 wherein said compound is L-prolyl-D-N-methyl-leucine ethylamide.

* * * * *